(12) United States Patent
Ding et al.

(10) Patent No.: US 12,209,101 B2
(45) Date of Patent: *Jan. 28, 2025

(54) PROLYL HYDROXYLASE DOMAIN-CONTAINING PROTEIN (PHD) INHIBITORS AND USES THEREOF

(71) Applicant: Insilico Medicine IP Limited, Hong Kong (HK)

(72) Inventors: Xiao Ding, Shanghai (CN); Liena Qin, Shanghai (CN); Feng Ren, Shanghai (CN); Jianyu Xu, Shanghai (CN)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,886

(22) Filed: Aug. 31, 2023

(65) Prior Publication Data

US 2024/0067661 A1    Feb. 29, 2024

Related U.S. Application Data

(63) Continuation of application No. 18/110,261, filed on Feb. 15, 2023, now Pat. No. 11,780,854, which is a continuation of application No. PCT/CN2022/128220, filed on Oct. 28, 2022.

(30) Foreign Application Priority Data

Oct. 28, 2021  (WO) ............... PCT/CN2021/127023
Aug. 12, 2022  (WO) ............... PCT/CN2022/112270

(51) Int. Cl.
  *C07D 519/00*   (2006.01)
  *C07D 471/04*   (2006.01)

(52) U.S. Cl.
  CPC ......... *C07D 519/00* (2013.01); *C07D 471/04* (2013.01)

(58) Field of Classification Search
  CPC .. C07D 519/00; C07D 471/04; C07D 487/04; A61P 1/00; A61P 7/06; C07F 9/6584
  See application file for complete search history.

(56) References Cited

U.S. PATENT DOCUMENTS

| 8,604,012 | B2 | 12/2013 | Klaus et al. |
| 8,609,646 | B2 | 12/2013 | Klaus et al. |
| 8,629,131 | B2 | 1/2014  | Klaus et al. |
| 8,962,530 | B2 | 2/2015  | Colgan |
| 9,920,011 | B2 | 3/2018  | Klaus et al. |
| 9,994,566 | B2 | 6/2018  | Zhou et al. |
| 11,731,987 | B2 | 8/2023  | Ding et al. |
| 11,780,854 | B2 | 10/2023 | Ding et al. |
| 2008/0146563 | A1 | 6/2008 | Eldred et al. |
| 2023/0192688 | A1 | 6/2023 | Ding et al. |
| 2024/0002406 | A1 | 1/2024 | Ding et al. |

FOREIGN PATENT DOCUMENTS

| CN | 108341777 A | 7/2018 |
| CN | 112979541 A | 6/2021 |
| WO | WO-0204443 A2 | 1/2002 |
| WO | WO-2004019933 A1 | 3/2004 |
| WO | WO-2009002533 A1 | 12/2008 |
| WO | WO-2009037570 A2 | 3/2009 |
| WO | WO-2011106226 A2 | 9/2011 |
| WO | WO-2013134660 A1 | 9/2013 |
| WO | WO-2016148306 A1 | 9/2016 |
| WO | WO-2016155357 A1 | 10/2016 |
| WO | WO-2016155358 A1 | 10/2016 |
| WO | WO-2018218042 A1 | 11/2018 |
| WO | WO-2019060850 A1 | 3/2019 |
| WO | WO-2019062733 A1 | 4/2019 |
| WO | WO-2020048380 A1 | 3/2020 |
| WO | WO-2021163344 A1 | 8/2021 |
| WO | WO-2021198709 A1 | 10/2021 |
| WO | WO-2023072240 A1 | 5/2023 |
| WO | WO-2023072246 A1 | 5/2023 |
| WO | WO-2023072257 A1 | 5/2023 |

OTHER PUBLICATIONS

Co-pending U.S. Appl. No. 18/339,362, inventors Ding; Xiao et al., filed Jun. 22, 2023.
PCT/CN2022/128220 International Search Report and Written Opinion dated Dec. 19, 2022.
PCT/CN2022/128237 International Search Report and Written Opinion dated Jan. 28, 2023.
PCT/CN2022/128293 International Search Report and Written Opinion dated Jan. 28, 2023.
U.S. Appl. No. 18/339,362 Office Action dated Jan. 2, 2024.
Co-pending U.S. Appl. No. 18/704,366, inventors Ding; Xiao et al., filed Apr. 24, 2024.
Co-pending U.S. Appl. No. 18/704,371, inventors Ding; Xiao et al., filed Apr. 24, 2024.

*Primary Examiner* — Susanna Moore
*Assistant Examiner* — Luisalberto Gonzalez
(74) *Attorney, Agent, or Firm* — WILSON SONSINI GOODRICH & ROSATI

(57) ABSTRACT

Described herein are PHD inhibitors and pharmaceutical compositions comprising said inhibitors. The subject compounds and compositions are useful for the treatment of anemia.

14 Claims, No Drawings

PROLYL HYDROXYLASE DOMAIN-CONTAINING PROTEIN (PHD) INHIBITORS AND USES THEREOF

This patent application is a continuation of U.S. application Ser. No. 18/110,261, filed Feb. 15, 2023, which is a continuation of International Application No. PCT/CN2022/128220, filed Oct. 28, 2022, which claims the benefit of International Application No. PCT/CN2021/127023, filed Oct. 28, 2021 and International Application No. PCT/CN2022/112270, filed Aug. 12, 2022; which are incorporated herein by reference in their entirety.

BACKGROUND

Hypoxia-inducible factor (HIF) mediates gene expression in response to changes in cellular oxygen concentration. HIF is a heterodimer having an oxygen-regulated subunit (HIF-α) and a constitutively expressed subunit (HIF-β). HIF prolyl hydroxylase, which is also known as prolyl hydroxylase domain-containing protein (PHD), exists as three isoforms in humans (PHD1, PHD2, and PHD3). PHDs act as oxygen sensors modulating the hypoxia-inducible factor ("HIF") degradation pathway. Briefly, PHDs are responsible for hydroxylation of HIFα, a subunit of HIF, which initiates the pathway that eventually results in the degradation of HIFα by the proteasome. There are three subtypes of PHDs, including PHD1, PHD2 and PHD3. Inhibition of PHDs has been indicated as a promising therapy for the HIFα related disease, such as anemia.

Inhibitors of PHDs coordinate erythropoiesis by inducing both renal and hepatic erythropoietin ("EPO") synthesis, which stimulates the production of red blood cells in the bone marrow, and by regulating the metabolism of iron, an indispensable component of functional red blood cells. Inhibitors of PHDs could also suppress the production of hepatic hepcidin, which has negative effects on iron mobilization. It is also speculated that inhibitors of PHDs might upregulate the expression several iron metabolism gene, such as DMT1 and DCYTB. Because of the central role HIF prolyl hydrolase plays in cellular oxygen sensing, inhibitors of PHD may be useful in treating cardiovascular disorders, metabolic disorders, hematological disorders, pulmonary disorders, kidney disorders, liver disorders, wound healing disorders, and cancer, among others.

SUMMARY

Disclosed herein is a compound of Formula (I), or a pharmaceutically acceptable salt, solvate, or stereoisomer thereof:

Formula (I)

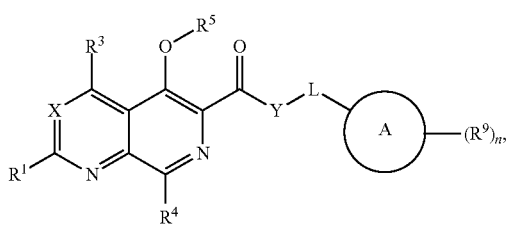

wherein:
$R^1$ is bicyclic heterocycloalkyl optionally and independently substituted with one or more $R^{1a}$;

each $R^{1a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^{1a}$ on the same atom are taken together to form an oxo;
X is N or CR$^2$;
$R^2$ is hydrogen, fluoro, chloro, bromo, —CN, —NO$_2$, —OH, —OR$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
$R^3$ is hydrogen, halogen, —CN, —NO$_2$, —OH, —OR$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
$R^4$ is hydrogen, halogen, —CN, —NO$_2$, —OH, —OR$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
$R^5$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
Y is —O—, —S—, or —NR$^6$—;
$R^6$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
L is —(CR$^7$R$^8$)$_p$—;
each $R^7$ and $R^8$ are independently hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
or $R^7$ and $R^8$ on the same carbon are taken together to form a cycloalkyl or heterocycloalkyl; each optionally substituted with one or more $R^{7a}$;
each $R^{7a}$ is independently halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
p is 0-4;
Ring A is cycloalkyl, heterocycloalkyl, aryl, or heteroaryl;
each $R^9$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more 129a;
or two $R^9$ on the same atom are taken together to form an oxo;
each $R^{9a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{9a}$ on the same atom are taken together to form an oxo;

n is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more R;

each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —O$C_1$-$C_6$alkyl, —S(=O)$C_1$-$C_6$alkyl, —S(=O)$_2$$C_1$-$C_6$alkyl, —S(=O)$_2$NH$_2$, —S(=O)$_2$NH$C_1$-$C_6$alkyl, —S(=O)$_2$N($C_1$-$C_6$alkyl)$_2$, —NH$_2$, —NH$C_1$-$C_6$alkyl, —N($C_1$-$C_6$alkyl)$_2$, —NHC(=O)O$C_1$-$C_6$alkyl, —C(=O)$C_1$-$C_6$alkyl, —C(=O)OH, —C(=O)O$C_1$-$C_6$alkyl, —C(=O)NH$_2$, —C(=O)N($C_1$-$C_6$alkyl)$_2$, —C(=O)NH$C_1$-$C_6$alkyl, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl; or two R on the same atom are taken together to form an oxo.

Also disclosed herein is a pharmaceutical composition comprising a therapeutically effective amount of a compound disclosed herein, or a pharmaceutically acceptable salt, solvate, or stereoisomer thereof, and a pharmaceutically acceptable excipient.

Also disclosed herein is a method of treating a disease or disorder in a subject, the method comprising administering to the subject a compound disclosed herein, or a pharmaceutically acceptable salt, solvate, or stereoisomer thereof, or a pharmaceutical composition disclosed herein, wherein the disease or disorder is anemia.

Also disclosed herein is a method of stabilizing hypoxia inducible factor (HIF) in a subject, the method comprising administering to the subject a compound disclosed herein, or a pharmaceutically acceptable salt, solvate, or stereoisomer thereof, or a pharmaceutical composition disclosed herein. In some embodiments, the HIF is HIF-1α.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, —COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms (e.g., $C_3$-$C_{15}$ fully saturated cycloalkyl or $C_3$-$C_{15}$ cycloalkenyl), from three to ten carbon atoms (e.g., $C_3$-$C_{10}$ fully saturated cycloalkyl or $C_3$-$C_{10}$ cycloalkenyl), from three to eight carbon atoms (e.g., $C_3$-$C_8$ fully saturated cycloalkyl or $C_3$-$C_8$ cycloalkenyl), from three to six carbon atoms (e.g., $C_3$-$C_6$ fully saturated cycloalkyl or $C_3$-$C_6$ cycloalkenyl), from three to five carbon atoms (e.g., $C_3$-$C_5$ fully saturated cycloalkyl or $C_3$-$C_5$ cycloalkenyl), or three to four carbon atoms (e.g., $C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_8$ fully saturated heterocycloalkyl or $C_2$-$C_8$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_6$ heterocycloalkenyl), from two to five carbon atoms (e.g., $C_2$-$C_5$ fully saturated heterocycloalkyl or $C_2$-$C_5$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzopyranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$—CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, four, or more substituents. In some embodiments, the subject group is optionally substituted with one, two, three or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

Compounds

Described herein are compounds of Formula (I), or a pharmaceutically acceptable salt, solvate, or stereoisomer thereof useful in the treatment of anemia.

Disclosed herein is a compound of Formula (I), or a pharmaceutically acceptable salt, solvate, or stereoisomer thereof:

Formula (I)

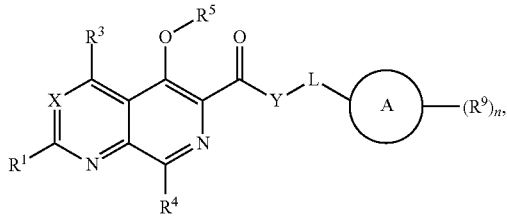

wherein:
R¹ is bicyclic heterocycloalkyl which is optionally and independently substituted;
X is N or CR²;
R² is hydrogen, fluoro, chloro, bromo, —CN, —NO₂, —OH, —OR$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
R³ is hydrogen, halogen, —CN, —NO₂, —OH, —OR$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
R⁴ is hydrogen, halogen, —CN, —NO₂, —OH, —OR$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
R⁵ is hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
Y is —O—, —S—, or —NR⁶—;
R⁶ is hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
L is —(CR⁷R⁸)$_p$—;
each R⁷ and R⁸ are independently hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
or R⁷ and R⁸ on the same carbon are taken together to form a cycloalkyl or heterocycloalkyl; each optionally substituted with one or more R$^{7a}$;
each R$^{7a}$ is independently halogen, —CN, —NO₂, —OH, —OR$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
p is 0-4;
Ring A is cycloalkyl, heterocycloalkyl, aryl, or heteroaryl;
each R⁹ is independently halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^b$C(=O)NR$^c$R$^d$, —NR$^b$C(=O)R$^a$, —R$^b$C(=O)OR$^b$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted;
n is 0-4;
each R$^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted;
each R$^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted; and
each R$^c$ and R$^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted;
or R$^c$ and R$^d$ are taken together with the atom to which they are attached to form an optionally substituted heterocycloalkyl.

Disclosed herein is a compound of Formula (I), or a pharmaceutically acceptable salt, solvate, or stereoisomer thereof:

Formula (I)

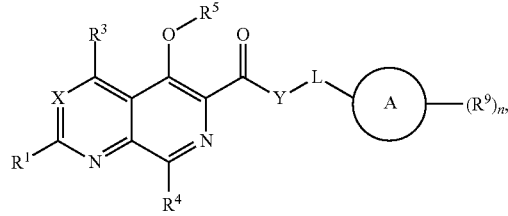

wherein:
R¹ is bicyclic heterocycloalkyl optionally and independently substituted with one or more R$^{1a}$;
each R$^{1a}$ is independently halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;
or two R$^{1a}$ on the same atom are taken together to form an oxo;
X is N or CR²;
R² is hydrogen, fluoro, chloro, bromo, —CN, —NO₂, —OH, —OR$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
R³ is hydrogen, halogen, —CN, —NO₂, —OH, —OR$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

$R^4$ is hydrogen, halogen, —CN, —NO$_2$, —OH, —OR$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

$R^5$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

Y is —O—, —S—, or —NR$^6$—;

$R^6$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

L is —(CR$^7$R$^8$)$_p$—;

each $R^7$ and $R^8$ are independently hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

or $R^7$ and $R^8$ on the same carbon are taken together to form a cycloalkyl or heterocycloalkyl; each optionally substituted with one or more $R^{7a}$;

each $R^{7a}$ is independently halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

p is 0-4;

Ring A is cycloalkyl, heterocycloalkyl, aryl, or heteroaryl;

each $R^9$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{9a}$;

or two $R^9$ on the same atom are taken together to form an oxo;

each $R^{9a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^{9a}$ on the same atom are taken together to form an oxo;

n is 0-4;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more R; and each $R^c$ and $R^d$ are independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —OC$_1$-C$_6$alkyl, —S(=O)C$_1$-C$_6$alkyl, —S(=O)$_2$C$_1$-C$_6$alkyl, —S(=O)$_2$NH$_2$, —S(=O)$_2$NHC$_1$-C$_6$alkyl, —S(=O)$_2$N(C$_1$-C$_6$alkyl)$_2$, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(=O)NHC$_1$-C$_6$alkyl, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl; or two R on the same atom are taken together to form an oxo.

In some embodiments of a compound of Formula (I), or a pharmaceutically acceptable salt, solvate, or stereoisomer thereof, X is N. In some embodiments of a compound of Formula (I), or a pharmaceutically acceptable salt, solvate, or stereoisomer thereof, X is CR$^2$.

In some embodiments of a compound of Formula (I), or a pharmaceutically acceptable salt, solvate, or stereoisomer thereof, $R^2$ is hydrogen, fluoro, or C$_1$-C$_6$alkyl. In some embodiments of a compound of Formula (I), or a pharmaceutically acceptable salt, solvate, or stereoisomer thereof, $R^2$ is hydrogen or C$_1$-C$_6$alkyl. In some embodiments of a compound of Formula (I), or a pharmaceutically acceptable salt, solvate, or stereoisomer thereof, $R^2$ is hydrogen.

In some embodiments of a compound of Formula (I), or a pharmaceutically acceptable salt, solvate, or stereoisomer thereof, $R^3$ is hydrogen, halogen, C$_1$-C$_6$alkyl, or C$_1$-C$_6$haloalkyl. In some embodiments of a compound of Formula (I), or a pharmaceutically acceptable salt, solvate, or stereoisomer thereof, $R^3$ is hydrogen, halogen, or C$_1$-C$_6$alkyl. In some embodiments of a compound of Formula (I), or a pharmaceutically acceptable salt, solvate, or stereoisomer thereof, $R^3$ is hydrogen or C$_1$-C$_6$alkyl. In some embodiments of a compound of Formula (I), or a pharmaceutically acceptable salt, solvate, or stereoisomer thereof, $R^3$ is hydrogen.

In some embodiments of a compound of Formula (I), or a pharmaceutically acceptable salt, solvate, or stereoisomer thereof, $R^4$ is hydrogen, halogen, C$_1$-C$_6$alkyl, or C$_1$-C$_6$haloalkyl. In some embodiments of a compound of Formula (I), or a pharmaceutically acceptable salt, solvate, or stereoisomer thereof, $R^4$ is hydrogen, halogen, or C$_1$-C$_6$alkyl. In some embodiments of a compound of Formula (I), or a pharmaceutically acceptable salt, solvate, or stereoisomer thereof, $R^4$ is hydrogen or C$_1$-C$_6$alkyl. In some embodiments of a compound of Formula (I), or a pharmaceutically acceptable salt, solvate, or stereoisomer thereof, $R^4$ is hydrogen.

In some embodiments of a compound of Formula (I), or a pharmaceutically acceptable salt, solvate, or stereoisomer thereof, $R^5$ is hydrogen or $C_1$-$C_6$alkyl. In some embodiments of a compound of Formula (I), or a pharmaceutically acceptable salt, solvate, or stereoisomer thereof, $R^5$ is $C_1$-$C_6$alkyl. In some embodiments of a compound of Formula (I), or a pharmaceutically acceptable salt, solvate, or stereoisomer thereof, $R^5$ is hydrogen.

In some embodiments of a compound of Formula (I), or a pharmaceutically acceptable salt, solvate, or stereoisomer thereof,

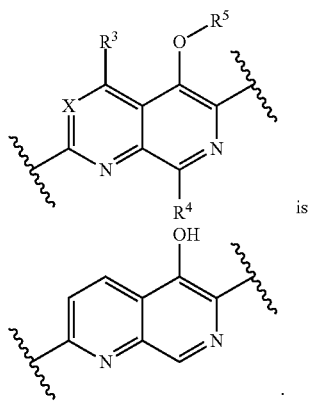

is

In some embodiments of a compound of Formula (I), or a pharmaceutically acceptable salt, solvate, or stereoisomer thereof,

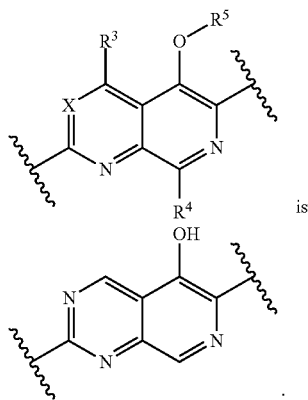

is

In some embodiments of a compound of Formula (I), or a pharmaceutically acceptable salt, solvate, or stereoisomer thereof, Y is —O— or —NR$^6$—. In some embodiments of a compound of Formula (I), or a pharmaceutically acceptable salt, solvate, or stereoisomer thereof, Y is —NR$^6$—. In some embodiments of a compound of Formula (I), or a pharmaceutically acceptable salt, solvate, or stereoisomer thereof, Y is —O—. In some embodiments of a compound of Formula (I), or a pharmaceutically acceptable salt, solvate, or stereoisomer thereof, Y is —S—.

In some embodiments of a compound of Formula (I), or a pharmaceutically acceptable salt, solvate, or stereoisomer thereof, $R^6$ is hydrogen or $C_1$-$C_6$alkyl. In some embodiments of a compound of Formula (I), or a pharmaceutically acceptable salt, solvate, or stereoisomer thereof, $R^6$ is $C_1$-$C_6$alkyl. In some embodiments of a compound of Formula (I), or a pharmaceutically acceptable salt, solvate, or stereoisomer thereof, $R^6$ is hydrogen.

In some embodiments of a compound of Formula (I), or a pharmaceutically acceptable salt, solvate, or stereoisomer thereof, p is 1-4. In some embodiments of a compound of Formula (I), or a pharmaceutically acceptable salt, solvate, or stereoisomer thereof, p is 1-3. In some embodiments of a compound of Formula (I), or a pharmaceutically acceptable salt, solvate, or stereoisomer thereof, p is 1 or 2. In some embodiments of a compound of Formula (I), or a pharmaceutically acceptable salt, solvate, or stereoisomer thereof, p is 1. In some embodiments of a compound of Formula (I), or a pharmaceutically acceptable salt, solvate, or stereoisomer thereof, p is 2. In some embodiments of a compound of Formula (I), or a pharmaceutically acceptable salt, solvate, or stereoisomer thereof, p is 3.

In some embodiments of a compound of Formula (I), or a pharmaceutically acceptable salt, solvate, or stereoisomer thereof, each $R^7$ and $R^8$ are independently hydrogen, $C_1$-$C_6$alkyl, $C_1$-$C_6$haloalkyl, or $C_1$-$C_6$hydroxyalkyl; or $R^7$ and $R^8$ on the same carbon are taken together to form a cycloalkyl or heterocycloalkyl. In some embodiments of a compound of Formula (I), or a pharmaceutically acceptable salt, solvate, or stereoisomer thereof, each $R^7$ and $R^8$ are independently hydrogen, $C_1$-$C_6$alkyl, $C_1$-$C_6$haloalkyl, or $C_1$-$C_6$hydroxyalkyl. In some embodiments of a compound of Formula (I), or a pharmaceutically acceptable salt, solvate, or stereoisomer thereof, $R^7$ and $R^8$ on the same carbon are taken together to form a cycloalkyl or heterocycloalkyl. In some embodiments of a compound of Formula (I), or a pharmaceutically acceptable salt, solvate, or stereoisomer thereof, each $R^7$ and $R^8$ are independently hydrogen or $C_1$-$C_6$alkyl. In some embodiments of a compound of Formula (I), or a pharmaceutically acceptable salt, solvate, or stereoisomer thereof, each $R^7$ and $R^8$ are hydrogen.

In some embodiments of a compound of Formula (I), or a pharmaceutically acceptable salt, solvate, or stereoisomer thereof, each $R^{7a}$ is independently halogen, —CN, —OH, —OR$^a$, —NR$^c$R$^d$, $C_1$-$C_6$alkyl, or $C_1$-$C_6$haloalkyl. In some embodiments of a compound of Formula (I), or a pharmaceutically acceptable salt, solvate, or stereoisomer thereof, each $R^{7a}$ is independently halogen, —OH, —OR$^a$, $C_1$-$C_6$alkyl.

In some embodiments of a compound of Formula (I), or a pharmaceutically acceptable salt, solvate, or stereoisomer thereof, Ring A is aryl or heteroaryl. In some embodiments of a compound of Formula (I), or a pharmaceutically acceptable salt, solvate, or stereoisomer thereof, Ring A is phenyl. In some embodiments of a compound of Formula (I), or a pharmaceutically acceptable salt, solvate, or stereoisomer thereof, Ring A is 5- or 6-membered heteroaryl. In some embodiments of a compound of Formula (I), or a pharmaceutically acceptable salt, solvate, or stereoisomer thereof, Ring A is 6-membered heteroaryl. In some embodiments of a compound of Formula (I), or a pharmaceutically acceptable salt, solvate, or stereoisomer thereof, Ring A is 6-membered pyridyl.

In some embodiments of a compound of Formula (I), or a pharmaceutically acceptable salt, solvate, or stereoisomer thereof, n is 1-3. In some embodiments of a compound of Formula (I), or a pharmaceutically acceptable salt, solvate, or stereoisomer thereof, n is 2-4. In some embodiments of a compound of Formula (I), or a pharmaceutically acceptable salt, solvate, or stereoisomer thereof, n is 2 or 3. In some embodiments of a compound of Formula (I), or a pharmaceutically acceptable salt, solvate, or stereoisomer thereof, n is 1 or 2. In some embodiments of a compound of Formula (I), or a pharmaceutically acceptable salt, solvate, or stereoisomer thereof, n is 0. In some embodiments of a compound of Formula (I), or a pharmaceutically acceptable salt, solvate, or stereoisomer thereof, n is 1. In some embodiments of a compound of Formula (I), or a pharmaceutically acceptable salt, solvate, or stereoisomer thereof, n is 2. In some embodiments of a compound of Formula (I), or a pharmaceutically acceptable salt, solvate, or stereoisomer thereof, n is 3.

In some embodiments of a compound of Formula (I), or a pharmaceutically acceptable salt, solvate, or stereoisomer thereof, each $R^9$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl.

In some embodiments of a compound of Formula (I), or a pharmaceutically acceptable salt, solvate, or stereoisomer thereof, each $R^9$ is independently halogen, —CN, —OH, —$OR^a$, —$NR^cR^d$, —C(=O)$OR^b$, $C_1$-$C_6$alkyl, or $C_1$-$C_6$haloalkyl.

In some embodiments of a compound of Formula (I), or a pharmaceutically acceptable salt, solvate, or stereoisomer thereof, each $R^9$ is independently halogen or —CN.

In some embodiments of a compound of Formula (I), or a pharmaceutically acceptable salt, solvate, or stereoisomer thereof, each $R^9$ is —CN.

In some embodiments of a compound of Formula (I), or a pharmaceutically acceptable salt, solvate, or stereoisomer thereof, $R^1$ is bicyclic heterocycloalkyl independently substituted with one or more $R^{1a}$. In some embodiments, $R^1$ is independently substituted with 1, 2, 3, or 4 $R^{1a}$. In some embodiments, $R^1$ is independently substituted with 1 or 2 $R^{1a}$. In some embodiments, $R^1$ is optionally substituted bicyclic heterocycloalkyl.

In some embodiments, $R^1$ is a spiro bicyclic heterocycloalkyl. In some embodiments, $R^1$ is a fused bicyclic heterocycloalkyl. In some embodiments, $R^1$ is a bridged bicyclic heterocycloalkyl. In some embodiments, $R^1$ is a 8-10 membered, optionally substituted bicyclic heterocycloalkyl. In some embodiments of a compound of Formula (I), or a pharmaceutically acceptable salt, solvate, or stereoisomer thereof, $R^1$ is

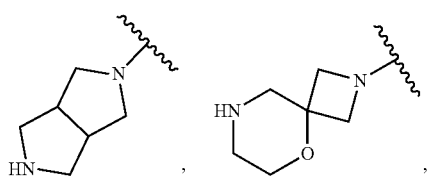

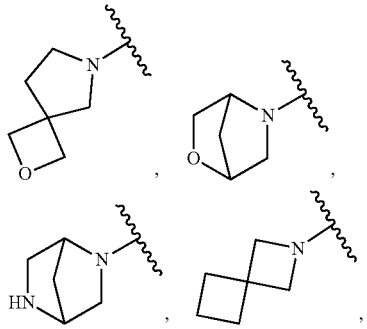

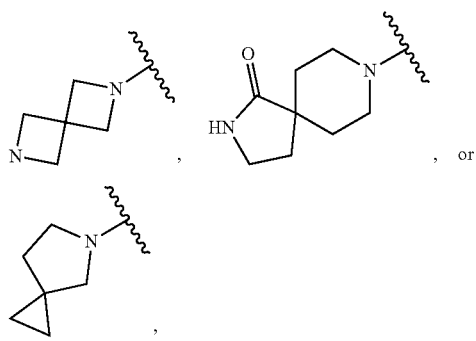

each of which is optionally substituted with one or more $R^{1a}$ (e.g., 1, 2, or 3 $R^{1a}$). In some embodiments, $R^1$ is

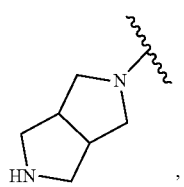 [SMILES: *N1CC2CNCC2C1]

which is unsubstituted or substituted with 1 or 2 $R^{1a}$. In some embodiments, $R^1$ is

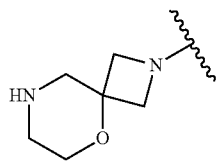

which is unsubstituted or substituted with 1 or 2 $R^{1a}$. In some embodiments, $R^1$ is

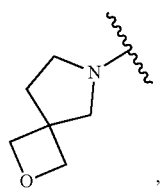 [SMILES: *N1CCC2(COC2)C1]

which is unsubstituted or substituted with 1 or 2 $R^{1a}$. In some embodiments, $R^1$ is

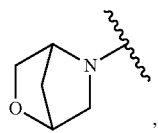 [SMILES: *N1CC2CC1CO2]

which is unsubstituted or substituted with 1 or 2 $R^{1a}$. In some embodiments, $R^1$ is

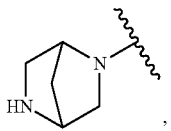

which is unsubstituted or substituted with 1 or 2 $R^{1a}$. In some embodiments, $R^1$ is

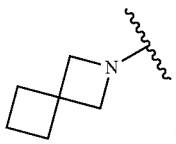

which is unsubstituted or substituted with 1 or 2 $R^{1a}$. In some embodiments, $R^1$ is

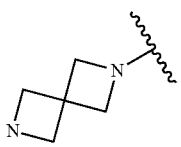

which is unsubstituted or substituted with 1 or 2 $R^{1a}$. In some embodiments, $R^1$ is

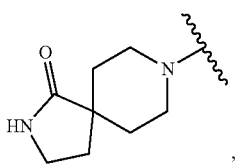

which is unsubstituted or substituted with 1 or 2 $R^{1a}$. In some embodiments, $R^1$ is

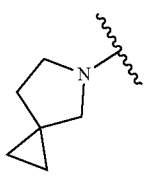

which is unsubstituted or substituted with 1 or 2 $R^{1a}$.

In some embodiments of a compound of Formula (I), or a pharmaceutically acceptable salt, solvate, or stereoisomer thereof, $R^1$ is 3,6-diazabicyclo[3.1.1]heptane, 2,5-diazabicyclo[2.2.1]heptane, 6-oxa-3-azabicyclo[3.1.1]heptane, or 2-oxa-5-azabicyclo[2.2.1]heptane, each optionally and independently substituted with one or more $R^{1a}$. In some embodiments of a compound of Formula (I), or a pharmaceutically acceptable salt, solvate, or stereoisomer thereof, $R^1$ is 2-oxa-5-azabicyclo[2.2.1]heptane optionally substituted with one or more $R^{1a}$.

In some embodiments of a compound of Formula (I), or a pharmaceutically acceptable salt, solvate, or stereoisomer thereof, $R^1$ is bicyclic heterocycloalkyl optionally and independently substituted with 1 or 2 $R^{1a}$. In some embodiments, $R^1$ is 7-9 membered bicyclic heterocycloalkyl optionally and independently substituted with 1 or 2 $R^{1a}$, and wherein the bicyclic heterocycloalkyl contains 0-1 ring oxygen and 1-2 ring nitrogen atoms.

In some embodiments of a compound of Formula (I), or a pharmaceutically acceptable salt, solvate, or stereoisomer thereof, $R^1$ is unsubstituted.

In some embodiments of a compound of Formula (I), or a pharmaceutically acceptable salt, solvate, or stereoisomer thereof, each $R^{1a}$ is independently halogen, —CN, —OH, —OR$^a$, —NR$^c$R$^d$, —NR$^b$C(=O)NR$^c$R$^d$, —NR$^b$C(=O)R$^a$, —NR$^b$C(=O)OR$^b$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; or two $R^{1a}$ on the same atom are taken together to form an oxo.

In some embodiments of a compound of Formula (I), or a pharmaceutically acceptable salt, solvate, or stereoisomer thereof, each $R^{1a}$ is independently halogen, —CN, —OH, —OR$^a$, —NR$^c$R$^d$, —NR$^b$C(=O)R$^a$, —NR$^b$C(=O)OR$^b$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; or two $R^{1a}$ on the same atom are taken together to form an oxo.

In some embodiments of a compound of Formula (I), or a pharmaceutically acceptable salt, solvate, or stereoisomer thereof, each $R^{1a}$ is independently halogen, —CN, —OH, —OR$^a$, —NR$^c$R$^d$, —NR$^b$C(=O)R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; or two $R^{1a}$ on the same atom are taken together to form an oxo.

In some embodiments of a compound of Formula (I), or a pharmaceutically acceptable salt, solvate, or stereoisomer thereof, each $R^{1a}$ is independently halogen, —OH, —OR$^a$, —NR$^b$C(=O)R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$heteroalkyl, or cycloalkyl; or two $R^{1a}$ on the same atom are taken together to form an oxo.

In some embodiments of a compound of Formula (I), or a pharmaceutically acceptable salt, solvate, or stereoisomer thereof, each $R^{1a}$ is independently $C_1$-$C_6$alkyl (e.g., methyl), $C_1$-$C_6$haloalkyl, or —C(=O)OR$^b$ (e.g., —C(=O)O($C_1$-$C_6$alkyl)).

In some embodiments of a compound of Formula (I), or a pharmaceutically acceptable salt, solvate, or stereoisomer thereof, $R^{1a}$ is —C(=O)NR$^c$R$^d$. In some embodiments of a compound of Formula (I), or a pharmaceutically acceptable salt, solvate, or stereoisomer thereof, $R^{1a}$ is —C(=O)NH$_2$. In some embodiments of a compound of Formula (I), or a pharmaceutically acceptable salt, solvate, or stereoisomer thereof, $R^{1a}$ is

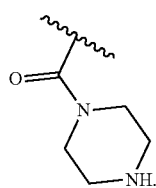 [SMILES: *C(=O)N1CCNCC1]

In some embodiments of a compound of Formula (I), or a pharmaceutically acceptable salt, solvate, or stereoisomer thereof, $R^1$ is

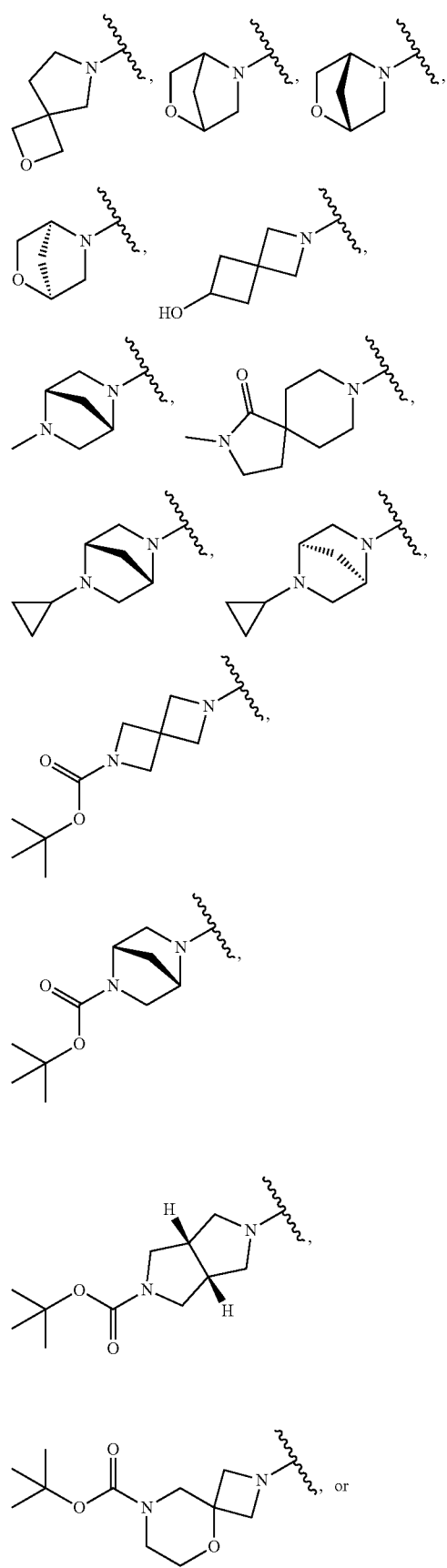
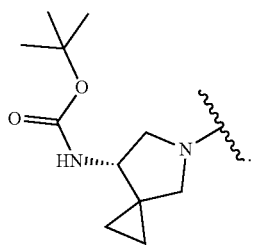
In some embodiments of a compound of Formula (I), or a pharmaceutically acceptable salt, solvate, or stereoisomer thereof, $R^1$ is
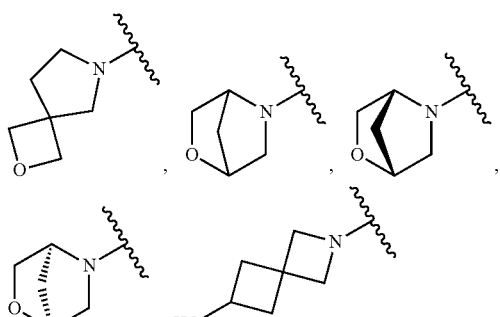
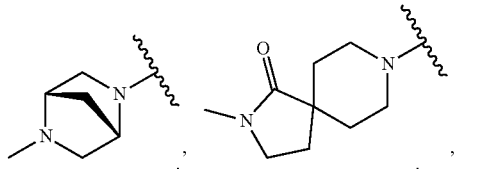
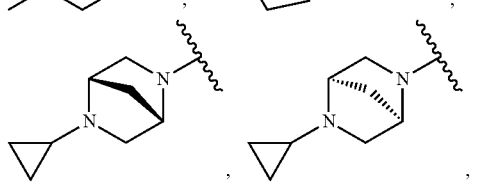
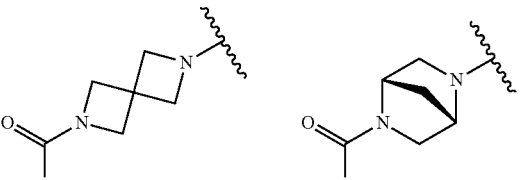
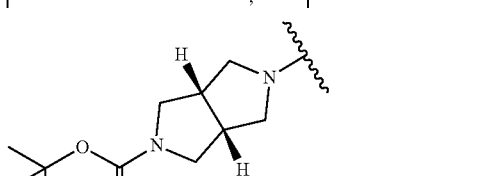
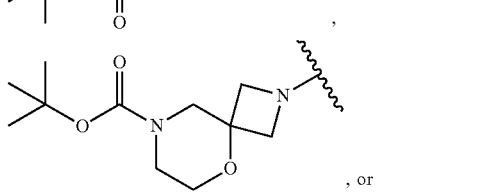
, or 23
-continued

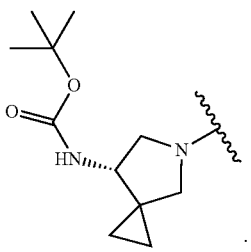

In some embodiments of a compound of Formula (I), or a pharmaceutically acceptable salt, solvate, or stereoisomer thereof, $R^1$ is

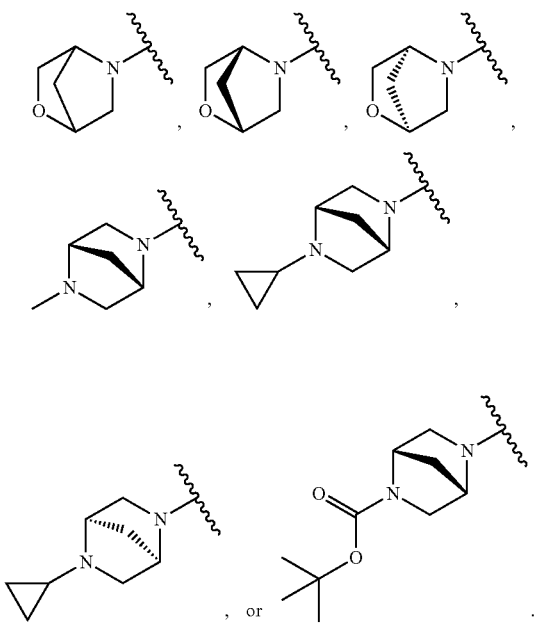

, or

In some embodiments of a compound of Formula (I), or a pharmaceutically acceptable salt, solvate, or stereoisomer thereof, $R^1$ is

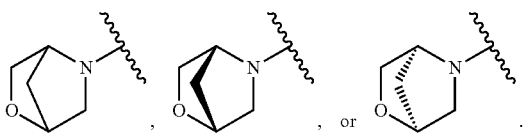 [SMILES: *N1CC2CC1CO2 ; *N1C[C@H]2C[C@@H]1CO2 ; *N1C[C@@H]2C[C@H]1CO2]

, or

In some embodiments of a compound of Formula (I), or a pharmaceutically acceptable salt, solvate, or stereoisomer thereof, $R^1$ is

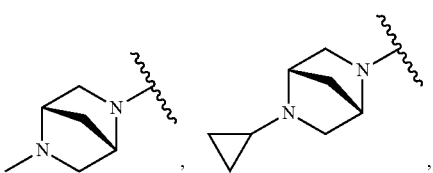

24
-continued

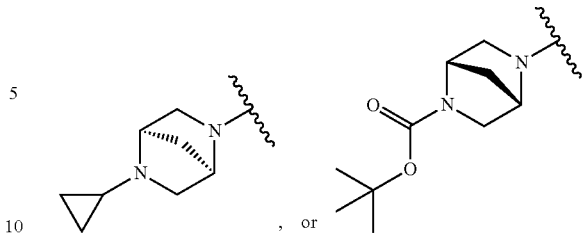

, or

In some embodiments of a compound of Formula (I), or a pharmaceutically acceptable salt, solvate, or stereoisomer thereof, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, cycloalkyl, heterocycloalkyl, aryl, and heteroaryl is independently optionally substituted with one or more R. In some embodiments of a compound of Formula (I), or a pharmaceutically acceptable salt, solvate, or stereoisomer thereof, each $R^a$ is independently $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound of Formula (I), or a pharmaceutically acceptable salt, solvate, or stereoisomer thereof, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (I), or a pharmaceutically acceptable salt, solvate, or stereoisomer thereof, each $R^a$ is independently $C_1$-$C_6$alkyl, $C_1$-$C_6$haloalkyl, or cycloalkyl, heterocycloalkyl. In some embodiments of a compound of Formula (I), or a pharmaceutically acceptable salt, solvate, or stereoisomer thereof, each $R^a$ is independently $C_1$-$C_6$alkyl or $C_1$-$C_6$haloalkyl. In some embodiments of a compound of Formula (I), or a pharmaceutically acceptable salt, solvate, or stereoisomer thereof, each $R^a$ is independently $C_1$-$C_6$alkyl.

In some embodiments of a compound of Formula (I), or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, cycloalkyl, heterocycloalkyl, aryl, and heteroaryl is independently optionally substituted with one or more R. In some embodiments of a compound of Formula (I), or a pharmaceutically acceptable salt, solvate, or stereoisomer thereof, each $R^b$ is independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound of Formula (I), or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (I), or a pharmaceutically acceptable salt, solvate, or stereoisomer thereof, each $R^b$ is independently hydrogen, $C_1$-$C_6$alkyl, $C_1$-$C_6$haloalkyl, or cycloalkyl, heterocycloalkyl. In some embodiments of a compound of Formula (I), or a pharmaceutically acceptable salt, solvate, or stereoisomer thereof, each $R^b$ is independently hydrogen, $C_1$-$C_6$alkyl or $C_1$-$C_6$haloalkyl. In some embodiments of a compound of Formula (I), or a pharmaceutically acceptable salt, solvate, or stereoisomer thereof, each $R^b$ is independently hydrogen or $C_1$-$C_6$alkyl. In some embodiments of a compound of Formula (I), or a pharmaceutically acceptable salt, solvate, or stereoisomer thereof, each $R^b$ is hydrogen. In some embodiments of a compound of Formula (I), or a pharmaceutically acceptable salt, solvate, or stereoisomer thereof, each $R^b$ is independently $C_1$-$C_6$alkyl.

In some embodiments of a compound of Formula (I), or a pharmaceutically acceptable salt, solvate, or stereoisomer thereof, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, cycloalkyl, heterocycloalkyl, aryl, and heteroaryl is independently optionally substituted with one or more R. In some embodiments of a compound of Formula (I), or a pharmaceutically acceptable salt, solvate, or stereoisomer thereof, each $R^c$ and $R^d$ are independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound of Formula (I), or a pharmaceutically acceptable salt, solvate, or stereoisomer thereof, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound of Formula (I), or a pharmaceutically acceptable salt, solvate, or stereoisomer thereof, each $R^c$ and $R^d$ are independently hydrogen, $C_1$-$C_6$alkyl, $C_1$-$C_6$haloalkyl, or cycloalkyl, heterocycloalkyl. In some embodiments of a compound of Formula (I), or a pharmaceutically acceptable salt, solvate, or stereoisomer thereof, each $R^c$ and $R^d$ are independently hydrogen, $C_1$-$C_6$alkyl or $C_1$-$C_6$haloalkyl. In some embodiments of a compound of Formula (I), or a pharmaceutically acceptable salt, solvate, or stereoisomer thereof, each $R^c$ and $R^d$ are independently hydrogen or $C_1$-$C_6$alkyl. In some embodiments of a compound of Formula (I), or a pharmaceutically acceptable salt, solvate, or stereoisomer thereof, each $R^c$ and $R^d$ are hydrogen. In some embodiments of a compound of Formula (I), or a pharmaceutically acceptable salt, solvate, or stereoisomer thereof, each $R^c$ and $R^d$ are independently $C_1$-$C_6$alkyl. In some embodiments of a compound of Formula (I), or a pharmaceutically acceptable salt, solvate, or stereoisomer thereof, $R^c$ is hydrogen, $C_1$-$C_6$hydroxyalkyl, $C_1$-$C_6$alkyl, $C_1$-$C_6$aminoalkyl, or $C_1$-$C_6$haloalkyl. In some embodiments of a compound of Formula (I), or a pharmaceutically acceptable salt, solvate, or stereoisomer thereof, $R^d$ is hydrogen, $C_1$-$C_6$hydroxyalkyl, $C_1$-$C_6$alkyl, $C_1$-$C_6$haloalkyl, $C_1$-$C_6$aminoalkyl, $C_1$-$C_6$heteroalkyl, cycloalkyl, heterocycloalkyl, $C_1$-$C_6$alkylene(cycloalkyl), or $C_1$-$C_6$alkylene(heterocycloalkyl). In some embodiments of a compound of Formula (I), or a pharmaceutically acceptable salt, solvate, or stereoisomer thereof, $R^d$ is —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, —CH$_2$CH$_2$N(CH$_3$)$_2$, —CH$_2$CH$_2$OH, or —CH$_2$CH$_2$NHC(=O)O-t-butyl.

In some embodiments of a compound of Formula (I), or a pharmaceutically acceptable salt, solvate, or stereoisomer thereof, $R^c$ and $R^d$ are taken together with the atom to which they are attached to form a heterocycloalkyl optionally substituted with one or more R.

In some embodiments of a compound of Formula (I), or a pharmaceutically acceptable salt, solvate, or stereoisomer thereof, each R is independently halogen, —CN, —OH, —OC$_1$-C$_6$alkyl, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(=O)NHC$_1$-C$_6$alkyl, C$_1$-C$_6$alkyl, or C$_1$-C$_6$haloalkyl. In some embodiments of a compound of Formula (I), or a pharmaceutically acceptable salt, solvate, or stereoisomer thereof, each R is independently halogen, —CN, —OH, —OC$_1$-C$_6$alkyl, —NH$_2$, —C(=O)C$_1$-C$_6$alkyl, —C(=O)OH, —C(=O)OC$_1$-C$_6$alkyl, —C(=O)NH$_2$, C$_1$-C$_6$alkyl, or C$_1$-C$_6$haloalkyl. In some embodiments of a compound of Formula (I), or a pharmaceutically acceptable salt, solvate, or stereoisomer thereof, each R is independently halogen, —CN, —OH, —OC$_1$-C$_6$alkyl, —NH$_2$, C$_1$-C$_6$alkyl, or C$_1$-C$_6$haloalkyl.

In some embodiments of a compound disclosed herein, each $R^1$, $R^9$, $R^a$, $R^b$, $R^c$, $R^d$, the heterocycloalkyl formed when $R^7$ and $R^8$ are taken together, and the heterocycloalkyl formed when $R^c$ and $R^d$ are taken together, is optionally and independently substituted with one, two, three, or four substituents as defined herein. In some embodiments of a compound disclosed herein, each $R^1$, $R^9$, $R^a$, $R^b$, $R^c$, $R^d$, the heterocycloalkyl formed when $R^7$ and $R^8$ are taken together, and the heterocycloalkyl formed when $R^c$ and $R^d$ are taken together, is optionally and independently substituted with one, two, or three substituents as defined herein. In some embodiments of a compound disclosed herein, each $R^1$, $R^9$, $R^a$, $R^b$, $R^c$, $R^d$, the heterocycloalkyl formed when $R^7$ and $R^8$ are taken together, and the heterocycloalkyl formed when $R^c$ and $R^d$ are taken together, is optionally and independently substituted with one or two substituents as defined herein. In some embodiments of a compound disclosed herein, each $R^1$, $R^9$, $R^a$, $R^b$, $R^c$, $R^d$, the heterocycloalkyl formed when $R^7$ and $R^8$ are taken together, and the heterocycloalkyl formed when $R^c$ and $R^d$ are taken together, is optionally and independently substituted with one substituent as defined herein.

In some embodiments of a compound disclosed herein, the abundance of deuterium in each of R, $R^1$, $R^{1a}$, $R^2$, $R^3$, $R^4$, $R^5$, $R^6$, $R^7$, $R^{7a}$, $R^8$, $R^9$, $R^{9a}$, $R^a$, $R^b$, $R^c$, and/or $R^d$ is independently at least 1%, at least 10%, at least 20%, at least 30%, at least 40%, at least 50%, at least 60%, at least 70%, at least 80%, at least 90%, or 100% of a total number of hydrogen and deuterium.

In some embodiments of a compound disclosed herein, one or more of R, $R^1$, $R^{1a}$, $R^2$, $R^3$, $R^4$, $R^5$, $R^6$, $R^7$, $R^{7a}$, $R^8$, $R^9$, $R^{9a}$, $R^a$, $R^b$, $R^c$, and/or $R^d$ groups comprise deuterium at a percentage higher than the natural abundance of deuterium.

In some embodiments of a compound disclosed herein, one or more hydrogens are replaced with one or more deuteriums in one or more of the following groups R, $R^1$, $R^{1a}$, $R^2$, $R^3$, $R^4$, $R^5$, $R^6$, $R^7$, $R^{7a}$, $R^8$, $R^9$, $R^{9a}$, $R^a$, $R^b$, $R^c$, and/or $R^d$.

In some embodiments of a compound disclosed herein, one or more hydrogens of Ring A are replaced with one or more deuteriums.

Any combination of the groups described above for the various variables is contemplated herein. Throughout the specification, groups and substituents thereof are chosen by one skilled in the field to provide stable moieties and compounds.

In some embodiments the compound of Formula (I), or a pharmaceutically acceptable salt, solvate, or stereoisomer thereof, is one of the compounds in Table 1.

TABLE 1

| Ex. | Structure |
| --- | --- |
| 8 | 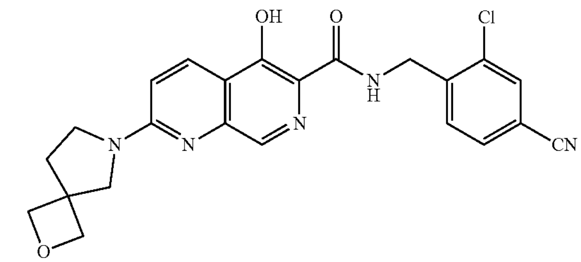 [SMILES: N#Cc1ccc(CNC(=O)c2ncc3nc(N4CCC5(COC5)C4)ccc3c2O)c(Cl)c1] |
| 25 | 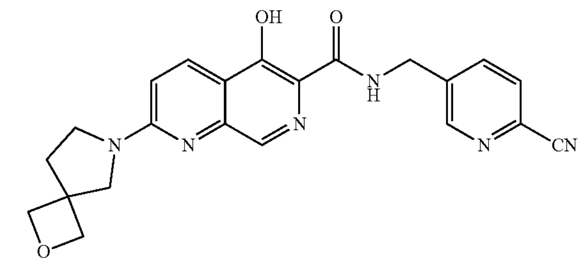 [SMILES: N#Cc1ccc(CNC(=O)c2ncc3nc(N4CCC5(COC5)C4)ccc3c2O)cn1] |
| 30 | 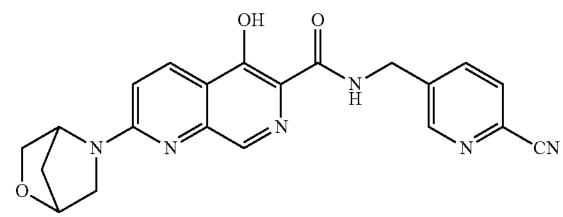 [SMILES: N#Cc1ccc(CNC(=O)c2ncc3nc(N4CC5CC4CO5)ccc3c2O)cn1] |
| 43 | 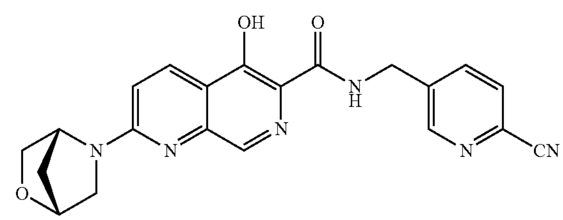 [SMILES: N#Cc1ccc(CNC(=O)c2ncc3nc(N4C[C@H]5C[C@@H]4CO5)ccc3c2O)cn1] |
| 44 | 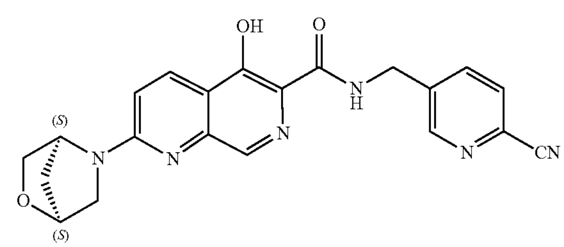 |
| 49 | 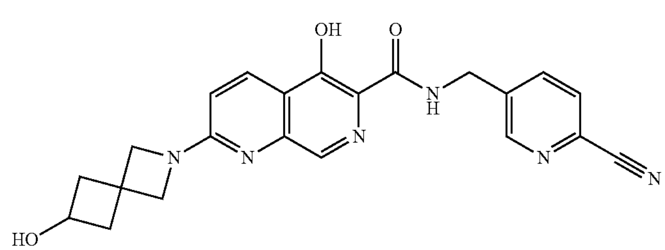 [SMILES: N#Cc1ccc(CNC(=O)c2ncc3nc(N4CC5(CC(O)C5)C4)ccc3c2O)cn1] |

TABLE 1-continued

| Ex. | Structure |
|---|---|
| 58 | 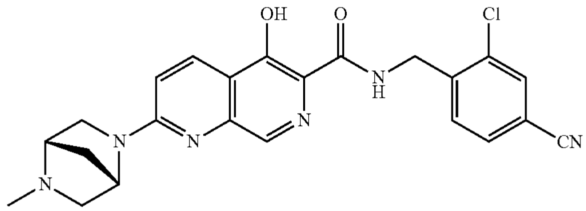 [SMILES: CN1C[C@@H]2C[C@H]1CN2c1ccc2c(O)c(C(=O)NCc3ccc(C#N)cc3Cl)ncc2n1] |
| 67 | 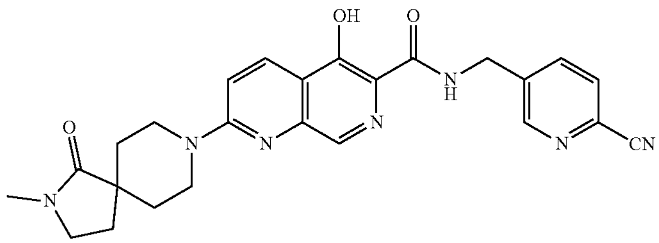 [SMILES: CN1CCC2(CCN(c3ccc4c(O)c(C(=O)NCc5ccc(C#N)nc5)ncc4n3)CC2)C1=O] |
| 68 | 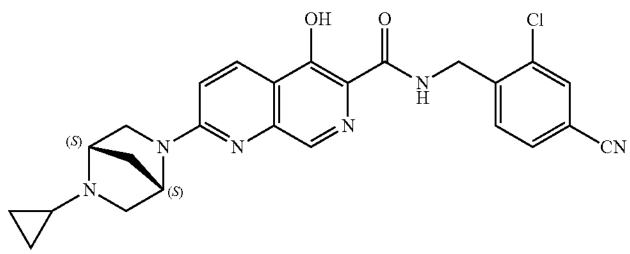 |
| 69 | 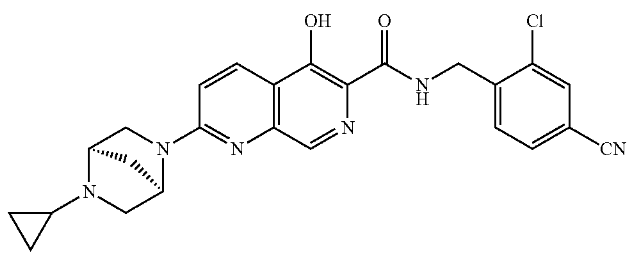 [SMILES: N#Cc1ccc(CNC(=O)c2ncc3nc(N4C[C@H]5C[C@@H]4CN5C4CC4)ccc3c2O)c(Cl)c1] |
| 80 | 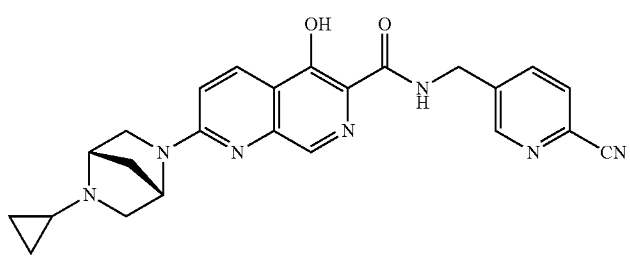 [SMILES: N#Cc1ccc(CNC(=O)c2ncc3nc(N4C[C@@H]5C[C@H]4CN5C4CC4)ccc3c2O)cn1] |
| 91 | 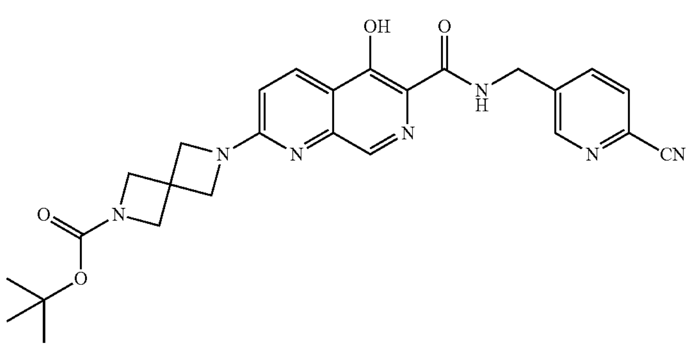 [SMILES: CC(C)(C)OC(=O)N1CC2(C1)CN(c1ccc3c(O)c(C(=O)NCc4ccc(C#N)nc4)ncc3n1)C2] |

TABLE 1-continued

| Ex. | Structure |
|---|---|
| 116 | 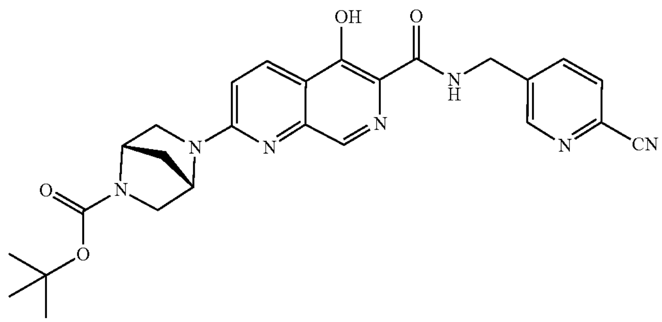 [SMILES: CC(C)(C)OC(=O)N1C[C@@H]2C[C@H]1CN2c1ccc2c(O)c(C(=O)NCc3ccc(C#N)nc3)ncc2n1] |
| 117 | 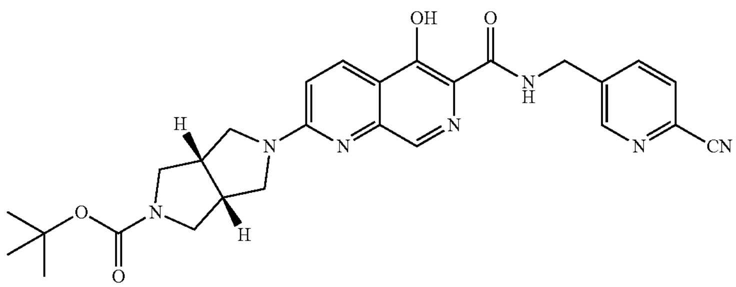 [SMILES: CC(C)(C)OC(=O)N1C[C@@H]2CN(c3ccc4c(O)c(C(=O)NCc5ccc(C#N)nc5)ncc4n3)C[C@@H]2C1] |
| 118 | 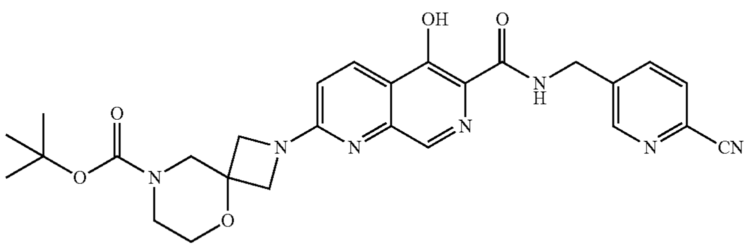 [SMILES: CC(C)(C)OC(=O)N1CCOC2(C1)CN(c1ccc3c(O)c(C(=O)NCc4ccc(C#N)nc4)ncc3n1)C2] |
| 145 | 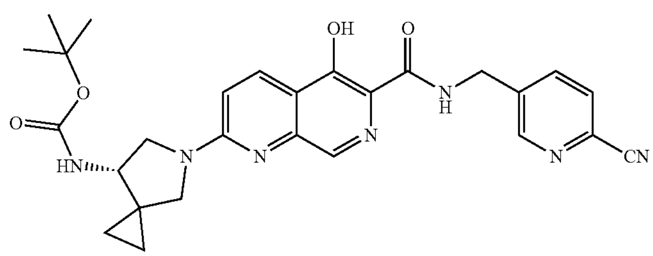 [SMILES: CC(C)(C)OC(=O)N[C@@H]1CN(c2ccc3c(O)c(C(=O)NCc4ccc(C#N)nc4)ncc3n2)CC12CC2] |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^2H$ (D), $^3H$ (T), $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability.

In some embodiments, the abundance of deuterium in each of the substituents disclosed herein is independently at least 1%, at least 10%, at least 20%, at least 30%, at least 40%, at least 50%, at least 60%, at least 70%, at least 80%, at least 90%, or 100% of a total number of hydrogen and deuterium. In some embodiments, one or more of the substituents disclosed herein comprise deuterium at a percentage higher than the natural abundance of deuterium. In some embodiments, one or more hydrogens are replaced with one or more deuteriums in one or more of the substituents disclosed herein.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4} alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein is a method of treating a disease or disorder in a subject, the method comprising administering to the subject a compound disclosed herein, or a pharmaceutically acceptable salt, solvate, or stereoisomer thereof, wherein the disease or disorder is anemia.

Anemia

Anemia is a frequent and serious complication of chronic kidney diseases with a relative deficiency in EPO production and a decrease in iron availability for hemoglobin ("Hb") synthesis. According to Informa, in 2020, there were 168 million prevalent cases of anemia resulted from chronic kidney diseases around the world. It is estimated that the number will rise to 182 million in 2027, according to the same source.

Currently, anemia resulting from chronic kidney diseases is managed by iron supplementation and, in more severe cases, by administration of supraphysiologic doses of erythropoiesis stimulating agents ("ESAs") in combination with adjuvant iron therapy. High doses of ESAs increase the risk of serious adverse events, including myocardial infarction, congestive heart failure, stroke, and death. Several inhibitors of PHDs have been launched and may serve as effective treatments for patients with anemia resulted from chronic kidney disease. However, the cardiovascular side effects caused by erythropoietin induction and potential off-target toxicities may raise safety concerns for long-term treatment. New therapies are needed to address both impaired EPO production and functional iron deficiency.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

EXAMPLES

Intermediate A: Synthesis of methyl 2-chloro-5-hydroxy-1,7-naphthyridine-6-carboxylate

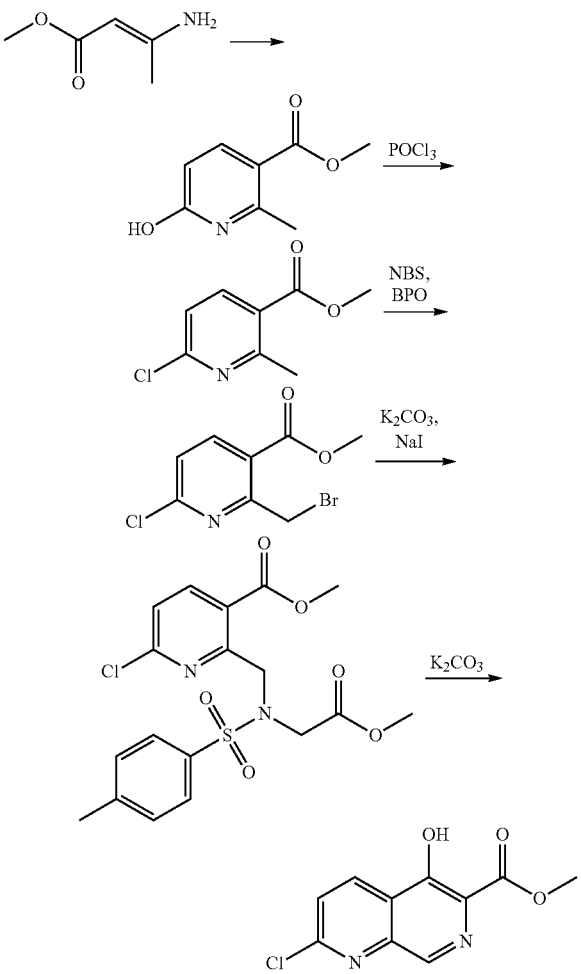

Step 1:
To a mixture of methyl (E)-3-aminobut-2-enoate (10 g, 87 mmol) in MeOH (100 mL) was added methyl prop-2-ynoate (7.78 g, 92.6 mmol). The mixture was stirred at 70° C. for 12 h. The mixture was cooled to 5° C. The precipitatie was filtered triturated with MTBE (50 mL×3). Methyl 6-hydroxy-2-methylnicotinate (5 g, 34% yield) was obtained as a white solid. NMR (400 MHz, CDCl$_3$) δ 12.61 (s, 1H), 8.02 (d, J=8 Hz, 1H), 6.42 (d, J=12 Hz, 1H), 3.84 (s, 3H), 2.72 (s, 3H).

Step 2:
A solution of mixture of methyl 6-hydroxy-2-methylnicotinate (5 g, 29.8 mmol) in POCl$_3$ (17.7 g, 115 mmol) was stirred at 100° C. for 4 h. The reaction was slowly poured into ice water (100 mL) and then extracted with ethyl acetate (100 mL×2). The combined organic layers were washed with NaHCO$_3$ (50 mL×2), dried over anhydrous Na$_2$SO$_4$, filtered and concentrated in vacuo. The crude was used directly for the next step.

Step 3:
To a solution of methyl 6-chloro-2-methylnicotinate (6 g, 32.4 mmol) in CCl$_4$ (60 mL) was added NBS (6.9 g, 38.7 mmol) and BPO (1.56 g, 6.45 mmol). The mixture was stirred at 80° C. for 12 h. The reaction mixture was diluted with DCM (60 mL) and washed with H₂O (60 mL×3). The organic layer was dried over MgSO₄, filtered, and concentrated under reduced pressure to give a residue. The residue was purified by silica gel chromatograph to afford Methyl 2-(bromomethyl)-6-chloronicotinate as a yellow solid (11 g, crude). LCMS: RT=0.981 min; MS m/z (ESI) [M+H]⁺ =264.1.

Step 4:

To a solution of methyl 2-(bromomethyl)-6-chloronicotinate (5 g, 18.9 mmol) and methyl 2-(p-tolylsulfonylamino)acetate (4.6 g, 18.9 mmol) in DMF (50 mL) was added K₂CO₃ (5.02 g, 47.4 mmol) and NaI (0.28 g, 1.86 mmol). The mixture was stirred at 50° C. for 12 h under N₂ atmosphere. The reaction mixture was diluted with ethyl acetate (200 mL) and washed with H₂O (80 mL×3). The organic layer was washed with brine (80 mL×3), dried over MgSO₄, filtered, and concentrated under reduced pressure to give a residue. The residue was purified by silica gel chromatograph to afford methyl 6-chloro-2-4(N-(2-methoxy-2-oxoethyl)-4-methylphenyl)sulfonamido)methypnicotinate (6 g, crude) as a yellow solid.

Step 5:

To a solution of methyl 6-chloro-2-(((N-(2-methoxy-2-oxoethyl)-4-methylphenyl)sulfonamido)methypnicotinate (6 g, 14 mmol) in DMSO (60 mL) was added K₂CO₃ (11.6 g, 84.3 mmol). The mixture was stirred at 50° C. for 4 h under N₂ atmosphere. The mixture was diluted with H₂O (60 mL) and the aqueous was adjusted pH to 6 with 1 M HCl. The precipitated solid was filtered and dried to afford Intermediate A (1.5 g, 45% yield) as an off-white solid. ¹H NMR (400 MHz, DMSO-d₆) δ 8.86 (s, 1H), 8.72 (d, J=0.9 Hz, 1H), 7.91 (d, J=8.8 Hz, 1H), 3.95 (s, 3H).

General Procedure A: The Synthesis of tert-butyl 4-(6-(((6-cyanopyridin-3-yl)methyl)carbamoyl)-5-hydroxy-1,7-naphthyridin-2-yl)piperazine-1-carboxylate

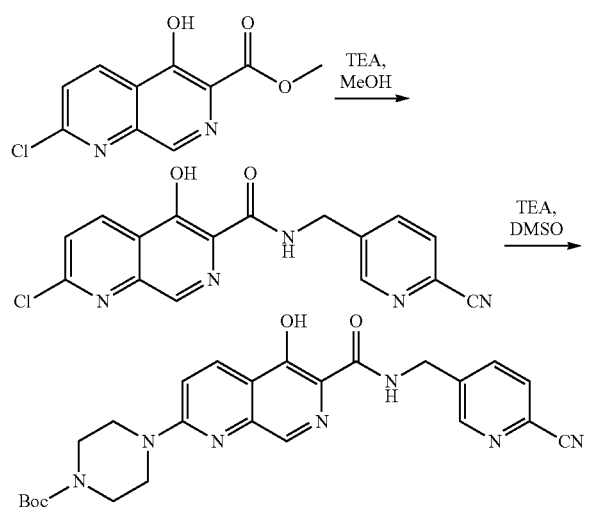

Step 1:

To a solution of Intermediate A (1 g, 4.19 mmol) in MeOH (30 mL) were added 5-(aminomethyl)pyridine-2-carbonitrile (0.84 g, 6.29 mmol), TEA (2.91 mL, 20.95 mmol), and the reaction was stirred at 75° C. overnight. The reaction mixture was filtered through normal funnel and the filter cake was washed with 10 mL MeOH, dried in vacuum to afford 2-chloro-N-((6-cyanopyridin-3-yl)methyl)-5-hydroxy-1,7-naphthyridine-6-carboxamide, Intermediate B (1.1 g, 3.24 mmol, 77% yield) as a yellow solid.

Step 2:

To a solution of Intermediate B (1.1 g, 3.24 mmol) in DMSO (15 mL) were added TEA (1.35 mL, 9.71 mmol), teat-butyl piperazine-1-carboxylate (904 mg, 4.86 mmol), and the reaction was stirred at 100° C. for 2 h under N₂. The reaction was cooled and poured into water H₂O (200 mL). The mixture was extracted with EtOAc (50 mL×3). The combined organic layer was washed with saturated NaCl solution (30 mL×3), and concentrated in vacuo. The residue was triturated with CH₃CN (20 mL) and CH₂Cl₂ (5 mL) and filtered to afford the title compound (500 mg, 1.02 mmol, 32% yield) as a white solid. LCMS: RT=1.838 min; MS m/z (ESI) [M+H]⁺=490.1. ¹H NMR (400 MHz, DMSO-d₆) δ 13.36 (s, 1H), 9.77 (t, J=6.3 Hz, 1H), 8.76 (s, 1H), 8.44 (s, 1H), 8.29 (d, J=9.4 Hz, 1H), 8.00 (s, 2H), 7.48 (d, J=9.5 Hz, 1H), 4.63 (d, J=6.3 Hz, 2H), 3.82-3.79 (m, 4H), 3.50-3.48 (m, 4H), 1.46 (s, 9H).

General Procedure D: The Synthesis of N-(2-chloro-4-cyanobenzyl)-5-hydroxy-2-(piperazin-1-yl)-1,7-naphthyridine-6-carboxamide

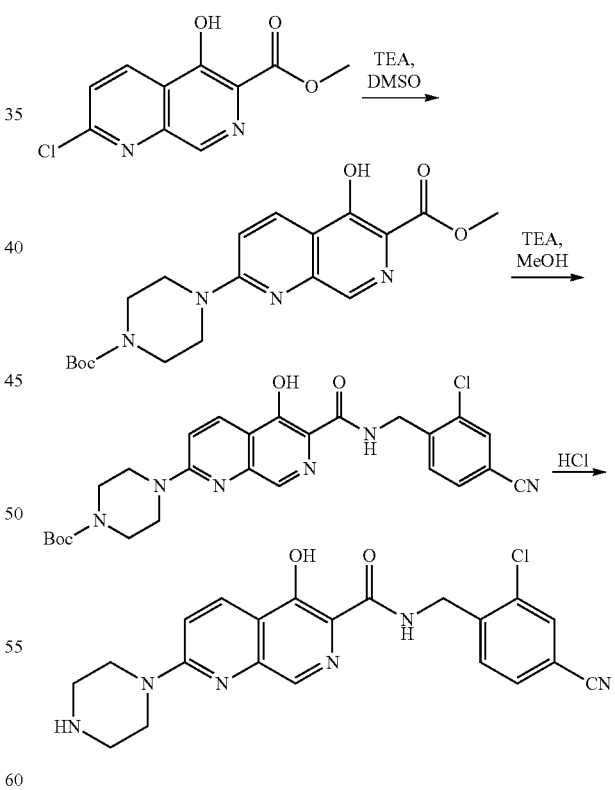

Step 1:

To a solution of Intermediate A (500 mg, 2.10 mmol) and teat-butyl piperazine-1-carboxylate (467.5 mg, 2.52 mmol) in anhydrous DMSO (5 mL) was added TEA (525 mg, 5.25 mmol). The solution was stirred at 100° C. for 16 h under N₂. The reaction mixture was poured into H₂O (30 mL) and extracted with ethyl acetate (30 mL×3). The combined organic layers were washed with brine (30 mL), dried over Na$_2$SO$_4$, filtered, and concentrated under reduced pressure. The residue was purified by flash silica gel chromatography. Methyl 2-(4-(tert-butoxycarbonyl)piperazin-1-yl)-5-hydroxy-1,7-naphthyridine-6-carboxylate (200 mg, 25% yield) was obtained as a yellow solid. LCMS: RT=1.002 min; MS m/z (ESI) [M+H]$^+$=389.0.

Step 2:

To a solution of methyl 2-(4-(tert-butoxycarbonyl)piperazin-1-yl)-5-hydroxy-1,7-naphthyridine-6-carboxylate (100 mg, 0.295 mmol) and 4-(aminomethyl)-3-chlorobenzonitrile (60 mg, 0.359 mmol) in anhydrous MeOH (1.5 mL) was added TEA (60 mg, 0.594 mmol). The solution was stirred at 75° C. for 20 h under N$_2$. The reaction mixture was concentrated under reduced pressure to remove solvent. The crude product (150 mg, crude, yellow oil) was directly put into the next step without further purification. LCMS: RT=1.097 min; MS m/z (ESI) [M+H]$^+$=523.4.

Step 3:

To a solution of the crude (150.0 mg, 0.287 mmol) in ethyl acetate (1.5 mL) was added a solution of 4N HCl/EtOAc (0.4 mL, 1.435 mmol). The solution was stirred at room temperature for 1.5 h. The reaction mixture was concentrated under reduced pressure to remove the solvent. The crude product was purified by prep-HPLC to afford the title compound (25.4 mg, 21% yield) as a white solid. LCMS: RT=2.217 min; MS m/z (ESI) [M+H]$^+$=423.2. $^1$H NMR (400 MHz, DMSO-d$_6$) δ 9.74 (s, 1H), 8.41 (s, 1H), 8.41-8.23 (m, 2H), 8.07-8.06 (m, 1H), 7.81-7.79 (m, 1H), 7.51-7.49 (m, 2H), 4.63-4.62 (m, 2H), 3.75-3.72 (m, 4H), 2.83- 2.80 (m, 4H).

The following compounds were made according to the general procedure as shown in the table 2 below:

TABLE 2

| Ex. | General procedure |
| --- | --- |
| 8 | D |
| 25 | D |
| 30 | D |
| 43 | D |
| 44 | A |
| 49 | A |
| 58 | A |
| 67 | A |
| 68 | A |
| 69 | A |
| 80 | A |
| 91 | A |
| 116 | A |
| 117 | A |
| 118 | A |
| 145 | A |

Biological Examples

Example A: PHD2 Enzymatic Assay Procedure

Compound DMSO stock preparation: All compounds were reconstituted into 20 mM stock by DMSO.

Compound storage: All compounds in DMSO were stored at RT in a desiccator for short-term storage (up to 3 months). Leftover compounds were store at −20 for longer term.

Working Stock Preparation:

Reference Roxadustat (FG-4592) was 3-fold serial diluted from 400 μM for 10 doses in DMSO.

The compounds were 3-fold serial diluted from 400 μM for 10 doses in DMSO.

Prepared 200×positive control (400 μM, FG-4592) and 200×vehicle control (100% DMSO).

Centrifuged compound plates at 1000 rpm for 1 min.

Compound Screening:

a) Transferred 40 nl compound dilutions into each well of assay plates using Echo 655;

b) Sealed the assay plate and centrifuge compound plates at 1000 rpm for 1 min.

c) Prepared and add 4 μL of the 2×PHD2 enzyme working solution to individual well of the assay plate.

d) Sealed the assay plate and centrifuge compound plates at 1000 rpm for 1 min. Incubate plate at RT for 30 min.

e) Prepared and add 4 μl 2×PHD2 substrate working solution to each well of the assay plate.

f) Prepared and added 4 μL 4×stop solution to the each well of the assay plate.

g) Prepared 4×detection solution with AlphaScreen Streptavidin Donor beads, AlphaScreen Protein A Acceptor beads and Hydroxy-HIF-1α (Pro564) (D43B5) XP® Rabbit mAb.

h) Added 4 μL 4×detection solution to the each well of the assay plate. repeat at step d.

i) Read Alphascreen signal on Envision HTS plate reader.

Data Analysis

ALPHASCREEN signal (ALPcmpd) is calculated for each well 2.2% Inhibition is calculated as follow:

$$\% \text{ Inhibition} = \left[1 - \frac{\overline{ALP}_{compound} - \overline{ALP}_{positive}}{\overline{ALP}_{vehicle} - \overline{ALP}_{positive}}\right] \times 100$$

$\overline{ALP}_{positive}$: The average ALP for the positive controls across the plate.

$\overline{ALP}_{vehicle}$: The average ALP for the negative controls across the plate.

2.3 Calculate IC$_{50}$ and Plot effect-dose curve of compounds:

Calculated IC$_{50}$ by fitting % inhibition values and log of compound concentrations to nonlinear regression (dose response–variable slope) with Graphpad 8.0.

$Y$=Bottom+(Top-Bottom)/(1+10^((LogIC50-X)*Hill-Slope))

X: log of Inhibitor concentration; Y: % Inhibition.

Example B: EPO Elisa Assay

The compounds powder were dissolved in 100% DMSO. The compounds stock solution were kept in nitrogen cabinet.

Experimental Methods

Cell seeding: Added 100 μl cell suspension contain 20k Hep3B cell per well.

Preparation of compound concentration gradient: Compounds at top dose of 100 μM, 3-fold dilution, 8 doses, singlet or duplicate. Prepare a solution of 200×the final concentration in a 96-well plate, dilute the compound by 200/3×with cell culture medium, and then pipette 50 μL to wells. Add 50 μL of culture medium containing DMSO to the minimum control well to make the final concentration contain 5‰ DMSO, and add 50 μL of the highest concentration of reference compound to the maximum control well, and incubate at 37° C. for 24 h.

Washed the reaction plate twice with 400 μl of 1×Wash Buffer per well.

Added 100 µL of the diluted standard (including standard blank control) to the appropriate wells.

Added 50 µL of sample and 50 µL of Sample Diluent to the sample well.

Added 50 µL 1×Biotin Conjugated Antibody to all wells and incubate for 1 hour at room temperature.

Washed the reaction plate 6 times with 400 µL 1×Wash Buffer per well.

Added 100 µL 1×Streptavidin-HRP to each well. Incubate at room temperature for 15 minutes.

Washed the reaction plate 6 times with 400 µL 1×Wash Buffer per well.

Added 100 µL TMB Substrate Solution to each well. Incubate at room temperature for 10 minutes.

Added 100 µL Stop Solution to each well.

Read OD450 with EnSight.

Data Analysis

Using GraphPad Prism 5.

% Act.=(Compound signal−Min signal)/(Max signal−Min signal)*100.

Max signal was obtained from the maximum control wells.

Min signal was obtained from the minimum control wells.

Take the log value of the concentration as the X-axis, and the percentage inhibition rate on the Y-axis. Use the analysis software GraphPad Prism 5 log(inhibitor) vs. response -Variable slope to fit the dose-response curve to obtain the $EC_{50}$ value of each compound.

The data from examples A and B are shown in Table 3.

TABLE 3

| Ex. | PHD2 | HEP3B EPO assay EC50 |
| --- | --- | --- |
| 8 | B | B |
| 25 | A | A |
| 30 |   | B |
| 43 | A | B |
| 44 | A | B |
| 48 | E | E |
| 58 | A | E |
| 67 | A | C |
| 68 | B | A |
| 69 | B | B |
| 80 | A | A |
| 91 | A | A |
| 116 | A | E |
| 117 | A | B |
| 118 | A | B |
| 145 | A | E |

PHD2 (nM): 0 < A ≤ 5; 5 < B ≤ 20; 20 < C ≤ 100; 100 < D ≤ 1,000; 1,000 < E ≤ 100,000
HEP3B EPO assay (EC50, nM): 0 < A ≤ 2,500; 2,500 < B ≤ 5,000; 5,000 < C ≤ 7500; 7,500 < D ≤ 10,000; 10,000 < E ≤ 100,000

What is claimed is:

1. A method for therapeutic treatment of anemia in a subject in need thereof, the method comprising administering to the subject a pharmaceutical composition comprising (i) an effective amount of a compound of Formula (I), or a pharmaceutically acceptable salt or stereoisomer thereof:

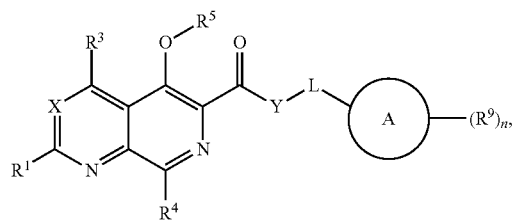

Formula (I)

wherein:
$R^1$ is

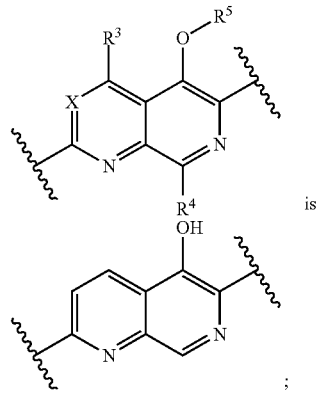

each of which optionally substituted with one or more $R^{1a}$;
each $R^{1a}$ is independently halogen, —CN, —OH, —$OR^a$, —$NR^cR^d$, —$NR^bC(=O)R^a$, —$C(=O)R^a$, —$C(=O)OR^b$, —$C(=O)NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl;
or two $R^{1a}$ on the same atom are taken together to form an oxo;

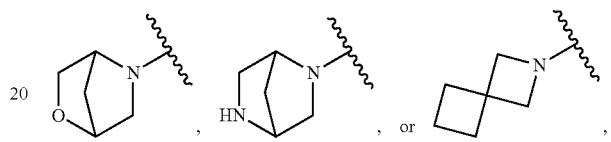

is

Y is —$NR^6$—;
$R^6$ is hydrogen;
L is —$(CR^7R^8)_p$—;
each $R^7$ and $R^8$ are hydrogen;
p is 1;
Ring A is aryl or heteroaryl;
each $R^9$ is independently halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;
n is 1 or 2;
each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more R;

each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —O$C_1$-$C_6$alkyl, —S(=O)$C_1$-$C_6$alkyl, —S(=O)$_2C_1$-$C_6$alkyl, —S(=O)$_2$NH$_2$, —S(=O)$_2$NH$C_1$-$C_6$alkyl, —S(=O)$_2$N($C_1$-$C_6$alkyl)$_2$, —NH$_2$, —NH$C_1$-$C_6$alkyl, —N($C_1$-$C_6$alkyl)$_2$, —NHC(=O)O$C_1$-$C_6$alkyl, —C(=O)$C_1$-$C_6$alkyl, —C(=O)OH, —C(=O)O$C_1$-$C_6$alkyl, —C(=O)NH$_2$, —C(=O)N($C_1$-$C_6$alkyl)$_2$, —C(=O)NH$C_1$-$C_6$alkyl, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl; or two R on the same atom are taken together to form an oxo; and (ii) a pharmaceutically acceptable excipient.

2. The method of claim 1, wherein in the compound of Formula (I), Ring A is phenyl.

3. The method of claim 1, wherein in the compound of Formula (I), Ring A is 6-membered heteroaryl.

4. The method of claim 1, wherein in the compound of Formula (I), n is 1.

5. The method of claim 1, wherein in the compound of Formula (I), each $R^9$ is independently halogen or —CN.

6. The method of claim 1, wherein in the compound of Formula (I), $R^1$ is

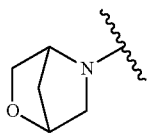

optionally substituted with one or more $R^{1a}$.

7. The method of claim 1, wherein in the compound of Formula (I), each $R^{1a}$ is independently halogen, —OH, —OR$^a$, —NR$^b$C(=O)R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$heteroalkyl, or cycloalkyl; or two $R^{1a}$ on the same atom are taken together to form an oxo.

8. The method of claim 1, wherein the compound of Formula (I) is selected from the group consisting of:

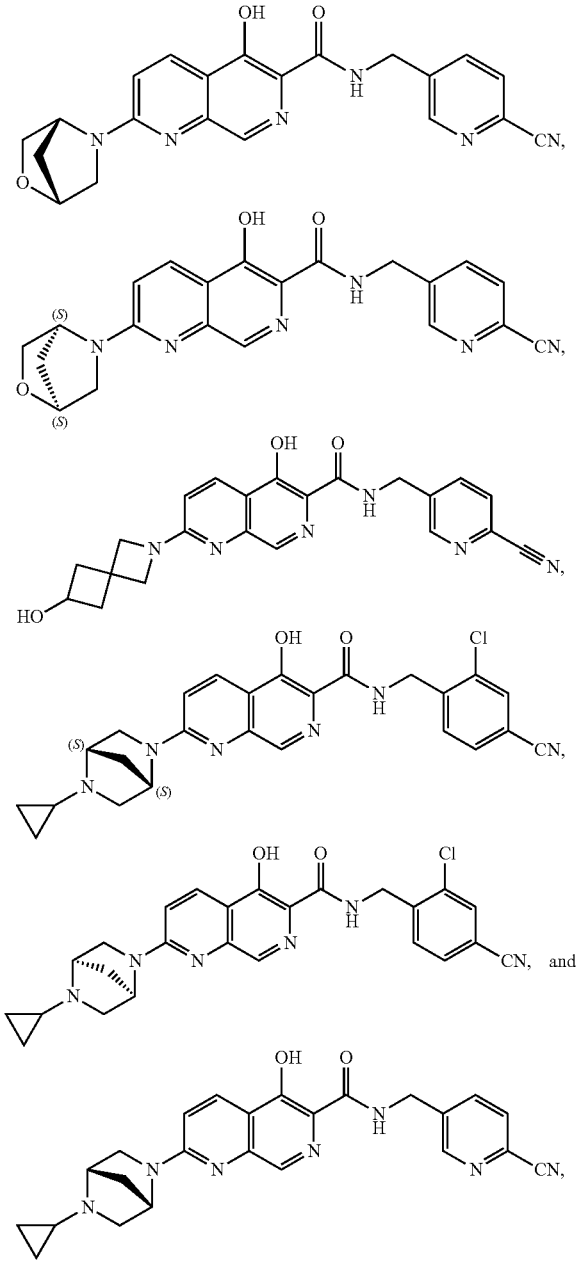

or a pharmaceutically acceptable salt or stereoisomer thereof.

9. The method of claim 8, wherein the compound of Formula (I) is:

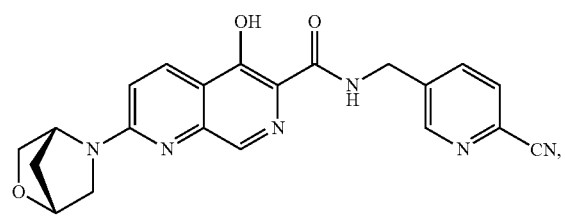 [SMILES: N#Cc1ccc(CNC(=O)c2ncc3nc(N4C[C@H]5C[C@@H]4CO5)ccc3c2O)cn1]

or a pharmaceutically acceptable salt or stereoisomer thereof.

10. The method of claim 8, wherein the compound of Formula (I) is:

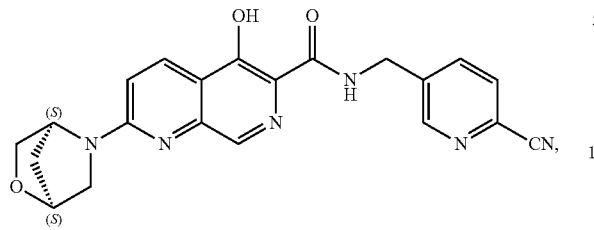

or a pharmaceutically acceptable salt or stereoisomer thereof.

11. The method of claim 8, wherein the compound of Formula (I) is:

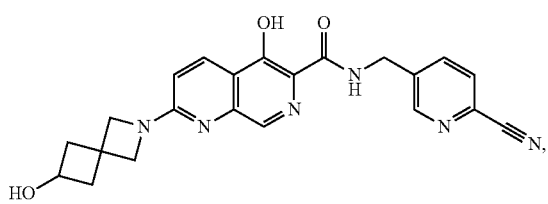 [SMILES: N#Cc1ccc(CNC(=O)c2ncc3nc(N4CC5(CC(O)C5)C4)ccc3c2O)cn1]

or a pharmaceutically acceptable salt or stereoisomer thereof.

12. The method of claim 8, wherein the compound of Formula (I) is:

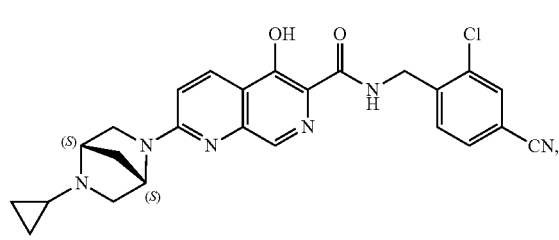

or a pharmaceutically acceptable salt or stereoisomer thereof.

13. The method of claim 8, wherein the compound of Formula (I) is:

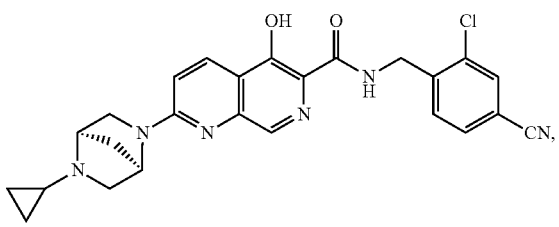 [SMILES: N#Cc1ccc(CNC(=O)c2ncc3nc(N4C[C@H]5C[C@@H]4CN5C4CC4)ccc3c2O)c(Cl)c1]

or a pharmaceutically acceptable salt or stereoisomer thereof.

14. The method of claim 8, wherein the compound of Formula (I) is:

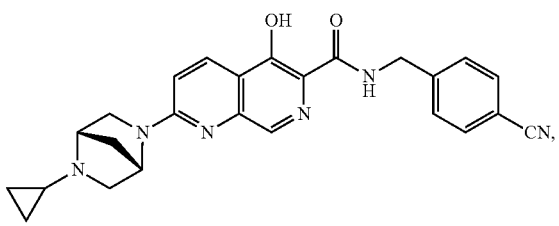 [SMILES: N#Cc1ccc(CNC(=O)c2ncc3nc(N4C[C@@H]5C[C@H]4CN5C4CC4)ccc3c2O)cc1]

or a pharmaceutically acceptable salt or stereoisomer thereof.

* * * * *